(12) United States Patent
Davis et al.

(10) Patent No.: US 9,174,908 B2
(45) Date of Patent: Nov. 3, 2015

(54) PROCESS FOR SEPARATING METHYLCYCLOPENTANONE FROM CYCLOHEXANONE

(71) Applicant: ExxonMobil Chemical Patents Inc., Baytown, TX (US)

(72) Inventors: Jason D. Davis, Humble, TX (US); Keith H. Kuechler, Friendswood, TX (US); James R. Lattner, LaPorte, TX (US); Christopher L. Becker, Manhattan, KS (US); John L. Heidman, Jr., Manassas, VA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/421,408

(22) PCT Filed: Sep. 6, 2013

(86) PCT No.: PCT/US2013/058535
§ 371 (c)(1),
(2) Date: Feb. 12, 2015

(87) PCT Pub. No.: WO2014/042993
PCT Pub. Date: Mar. 20, 2014

(65) Prior Publication Data
US 2015/0218076 A1    Aug. 6, 2015

Related U.S. Application Data

(60) Provisional application No. 61/701,156, filed on Sep. 14, 2012.

(30) Foreign Application Priority Data

Nov. 7, 2012 (EP) .................................. 12191520

(51) Int. Cl.
*C07C 45/82* (2006.01)
*C07C 2/68* (2006.01)
*C07C 45/80* (2006.01)
*C07C 45/28* (2006.01)
*C07D 223/10* (2006.01)
*B01D 3/14* (2006.01)

(52) U.S. Cl.
CPC ................ *C07C 45/80* (2013.01); *B01D 3/143* (2013.01); *C07C 45/28* (2013.01); *C07D 223/10* (2013.01)

(58) Field of Classification Search
CPC ............ C07C 45/53; C07C 45/82; C07C 2/66
USPC .......................... 568/346, 366, 798; 585/467
See application file for complete search history.

(56) References Cited

U.S. PATENT DOCUMENTS 6,037,513 A    3/2000   Chang et al.
6,245,907 B1   6/2001   Suh et al.

FOREIGN PATENT DOCUMENTS

CN    1226553    8/1999
EP    0 785 188  7/1997

*Primary Examiner* — Sikarl Witherspoon
(74) *Attorney, Agent, or Firm* — Siwen Chen (57) ABSTRACT

In a process for separating methylcyclopentanone from a mixture comprising methylcyclopentanone and cyclohexanone, a feedstock comprising cyclohexanone, methylcyclopentanone, water at a concentration of at least 0.10 wt %, and optionally phenol is fed into a fractionation distillation column, where a lower effluent rich in cyclohexanone and an upper effluent rich in methylcyclopentanone are produced. Due to the inclusion of water at a relatively high concentration in the feedstock, efficient separation of methylcyclopentanone is achieved. In certain particularly desirable embodiments, the lower effluent is substantially free of methylcyclopentanone. The thus produced cyclohexanone may be used to make, e.g., high-purity caprolactam, which, in turn, may be used for fabricating, e.g., high-performance nylon-6 material.

25 Claims, 1 Drawing Sheet

PROCESS FOR SEPARATING METHYLCYCLOPENTANONE FROM CYCLOHEXANONE

PRIORITY CLAIM

This application is a National Stage Application of International Application No. PCT/US2013/058535, filed Sep. 6, 2013, which claims the benefit of U.S. Provisional Application No. 61/701,156, filed Sep. 14, 2012, and European Application No. 12191520.1, filed Nov. 7, 2012, the disclosures of which are fully incorporated herein by their reference.

FIELD

The present invention relates to a process for separating methylcyclopentanone from a mixture of cyclohexanone and methylcyclopentanone. In particular, the present invention relates to a process for separating methylcyclopentanone from a mixture of cyclohexanone and methylcyclopentanone via fractionation using water as a separation promoting agent. The present invention is useful, e.g., in making high-purity cyclohexanone suitable for making high-purity caprolactam useful for fabricating high-performance nylon-6 polymer material.

BACKGROUND

Cyclohexanone is typically produced by the oxidation of cyclohexane, or the hydrogenation of phenol. These methods may also generate various contaminants that are difficult to separate from the desired products, and that can render the cyclohexanone product substandard or unusable to downstream processes, for example in the manufacture of caprolactam or adipic acid. Thus, certain treatment means have been described to remove those contaminants from cyclohexanone.

The production of phenol from cyclohexylbenzene is an emerging technology, interesting in that it co-produces cyclohexanone, rather than acetone. Cyclohexylbenzene may be produced, for example, by direct alkylation of benzene with cyclohexene, or as disclosed in U.S. Pat. No. 6,037,513, by contacting benzene with hydrogen in the presence of a catalyst. The cyclohexylbenzene may then be oxidized to the corresponding hydroperoxide and the hydroperoxide cleaved to phenol and cyclohexanone using a catalyst.

The production of phenol and cyclohexanone from cyclohexylbenzene also produces various contaminants that are difficult to separate from the desired products. However, the nature of those contaminants and the separations thereof are significantly different from those in the conventional Hock process for the production of phenol and acetone, and/or the conventional cyclohexanone production from cyclohexane or phenol. For example, hydroalkylation of benzene produces significant amounts of, among others, cyclohexane and lesser amounts of methylcyclopentane, cyclohexene, phenylcyclohexene, and phenylcyclohexyldiene. Similarly, the oxidation of cyclohexylbenzene typically produces peroxide species alien to the Hock process, such as the desired cyclohexyl-1-phenyl-1-hydroperoxide (CHBHP), and undesired byproduct hydroperoxides such as cyclohexyl-1-phenyl-2-hydroperoxide, cyclohexyl-1-phenyl-3-hydroperoxide and cyclohexyl-1-phenyl-4-hydroperoxide. The cleavage of these various hydroperoxides produces a wide variety of contaminant species which are not produced by the chemistry and technology of either the Hock process, the cyclohexane oxidation process, or the phenol hydrogenation process.

Caprolactam is an important industrial material for making nylon-6, a widely used polymer material. The purity of caprolactam has significant impact on the quality such as strength of nylon-6 made therefrom. Caprolactam can be made from cyclohexanone via the following Route-1:

(Route-1).

In the various industrial processes for making cyclohexanone, methylcyclopentanone may be produced as a contaminant. Even at a very small amount, such as on the level of several ppm, methylcyclopentanone, by undergoing similar reactions to those of cyclohexanone in reaction Route-1 above, may lead to the formation of highly undesirable contaminants, particularly methylvalerolactam having one or more of the following formulae:

(F-I)

(F-II)

(F-III)

and (F-IV)

Methylvalerolactam is very difficult to remove from caprolactam. During further reaction of caprolactam to produce nylon-6 via reaction Route-2 below:

(Route-2).

the various isomers of methylvalerolactam, shown above, by polymerization with each other and/or with caprolactam, may significantly reduce the quality and performance of the nylon-6 product, even if at a low concentration.

As such, there is a strong need of producing a cyclohexanone product with very low methylcyclopentanone concentration. Due to the very close boiling points of cyclohexanone (156° C. at 101 kPa), 2-methylcyclopentanone (140° C. at 101 kPa) and 3-methylcyclopentanone (145° C. at 101 kPa), separation of a physical mixture of cyclohexanone and methylcyclopentanone using traditional fractionation to purify cyclohexanone is quite difficult, especially if the concentration of methylcyclopentanone in the final cyclohexanone product is desired to be as low as several ppm by weight. Usually, this would entail the use of complicated, costly, and high maintenance equipment and processes such as one of more of (i) high vacuum inside the column; (ii) fractionation column with high number of distillation trays and/or a high reflux ratio; and (iii) multiple fractionation columns in a series to achieve the desired level of separation.

SUMMARY

The present inventors have found that by including water at a concentration of at least 0.10 wt % into the feedstock mixture of cyclohexanone and methylcyclopentanone, the separation efficiency may increase quite significantly. While without intending to be bound by any particular theory, it is believed that the inclusion of water at the amount disclosed herein may disrupt the interaction between the cyclohexanone and methylcyclopentanone molecules in the fractionation process at a significant level, resulting in a dramatic increase of separation efficiency in the fractionation process.

One aspect of the present disclosure relates to a process for separating methylcyclopentanone from a mixture comprising cyclohexanone and methylcyclopentanone, the process comprising:

(I) providing a first feedstock comprising cyclohexanone and methylcyclopentanone, the methylcyclopentanone having a concentration CMCP(1);

(II) including water in the first feedstock at a concentration CH2O(1) of at least 0.10 wt %; and (III) fractionating the first feedstock in a first distillation column to obtain a first upper effluent rich in methylcyclopentanone having a methylcyclopentanone concentration of CMCP(2) and a first lower effluent rich in cyclohexanone, wherein CMCP(2)/CMCP(1)≥3.0.

Another aspect of the present disclosure relates to a process for separating methylcyclopentanone from a mixture comprising cyclohexanone and methylcyclopentanone, the process comprising:

(A) providing a feed FEEDA comprising cyclohexanone, methylcyclopentanone, phenol, and a C12+ component;

(B) fractionating FEEDA in a first separation column to obtain:
an upper effluent EFFUB comprising cyclohexanone, methylcyclopentanone and phenol, and
a lower effluent EFFBB comprising at least a portion of the C12+ component;

(C) providing a feed FEEDC from at least a portion of EFFUB, FEEDC comprising water at a concentration CH2O(1) of at least 0.10 wt %, cyclohexanone, methylcyclopentanone at a concentration CMCP(1), and phenol; and (D) fractionating FEEDC in a second separation column to obtain:
an upper effluent EFFUD rich in methylcyclopentanone, and
a lower effluent EFFBD comprising cyclohexanone and phenol.

Embodiments of the processes of the present disclosure have one or more of the following advantages. First, by including a relatively large amount of water into the feedstock comprising cyclohexanone and methylcyclopentanone, the separation efficiency of methylcyclopentanone is enhanced significantly, enabling the enrichment of methylcyclopentanone in the upper effluent in a fractionation column with fewer theoretical trays, lower reflux ratio, and a lower methylcyclopentanone content in the lower effluent. Second, the present invention is especially useful for making cyclohexanone via the cyclohexylbenzene oxidation route. The processes of the present disclosure may be advantageously used in this process for removing methylcyclopentanone from cyclohexanone and phenol, enabling cost-effective production of high-purity cyclohexanone suitable for the production of high-purity caprolactam product used for making high-performance nylon-6 material starting from benzene hydroalkylation.

Additional features and advantages of the invention will be set forth in the detailed description and claims, as well as the appended drawings. It is to be understood that the foregoing general description and the following detailed description are merely exemplary of the invention, and are intended to provide an overview or framework to understanding the nature and character of the invention as it is claimed.

DETAILED DESCRIPTION OF THE EMBODIMENTS

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used. Likewise, "a C12+ component" should be interpreted to include one, two or more C12+ components unless specified or indicated by the context to mean only one specific C12+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first feedstock are expressed based on the total weight of the first feedstock. All ranges expressed herein should include both end points as two specific embodiments unless specified or indicated to the contrary.

As used herein, the term "methylcyclopentanone" includes both isomers 2-methylcyclopentanone (CAS registration No. 1120-72-5) and 3-methylcyclopentanone (CAS registration No. 1757-42-2), at any proportion between them, unless it is clearly specified to mean only one of these two isomers or the context clearly indicates that is the case. It should be noted that under the conditions of the various steps of the present processes, the two isomers may undergo isomerization reactions to result in a ratio between them different from that in the raw materials immediately before being charged into a vessel such as a fractionation column.

As used herein, the term "C12+ component" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding oxygenates such as alcohols, ketones, acids, and esters derived from these compounds.

As used herein, the term "feedstock" or "feed" means all raw materials in the aggregate charged into a vessel, such as a reactor or a separation device such as a fractionation column, at the same or different locations of the vessel. Thus, if all raw materials are mixed and charged into the vessel at a single inlet at a given location, the feedstock or feed means the single mixture charged into the vessel at the single inlet. For another example, if a first part of the raw materials with a first composition is charged into the vessel at a first inlet at a first location, and a second part of the raw materials with a second composition different from the first composition is charged into the vessel at a second inlet at a second location different from the first location, the feedstock includes both the first part and the second part.

An "upper effluent" as used herein may be at the very top or the side of a fractionation column, with or without an additional effluent above it. A "lower effluent" as used herein is at a location lower than the upper effluent, which may be at the very bottom or the side of a fractionation column, and if at the side, with or without additional effluent below it.

In the processes according to the first aspect of the present disclosure, described summarily above, FEEDA provided in step (A) comprises cyclohexanone at a concentration CHXN (A), methylcyclopentanone at a concentration CMCP(A), phenol at a concentration of CPhol(A) and a C12+ component, where the concentrations are based on the total weight of FEEDA. This feed FEEDA may be produced by various methods known in the art, e.g., (1) cyclohexane oxidation, such as the process described in U.S. Pat. No. 5,780,683; (2) hydrogenation of phenol, such as the process described in U.S. Pat. No. 8,222,459; or (3) cyclohexylbenzene oxidation followed by cleavage of the cyclohexylbenzene hydroperoxide, such as the process described in U.S. Pat. No. 6,037,513, or any combination thereof.

FEEDA may be an effluent from an upstream reactor without any purification or separation in certain embodiments, or a purified version thereof in other embodiments, or a synthetic mixture comprising components obtained from different sources in other embodiments. Thus, the concentration of cyclohexanone CHXN(A) in FEEDA may vary quite significantly, e.g., from 10 wt % to 99 wt %, based on the total weight of FEEDA. Non-limiting examples of CHXN(A), which may be the lower limit and/or upper limit of a range the actual CHXN(A) may fall within, include 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt % and 99 wt %. Likewise, the concentration of phenol CPhol(A) in FEEDA may vary quite significantly, e.g., from 5 wt % to 95 wt %. Non-limiting examples of CPhol(A), which may be the lower limit and/or upper limit of a range the actual CPhol(A) may fall within, include 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, and 95 wt %. The concentration of methylcyclopentanone CMCP (A) may vary quite significantly as well, e.g., from 1 ppm to 5 wt %. Desirably, CMCP(A) in FEEDA is not higher than 5 wt %. Non-limiting examples of CMCP(A), which may be the lower limit and/or upper limit of a range the actual CMCP(A) may fall within, include 1 ppm, 5 ppm, 10 ppm, 50 ppm, 100 ppm, 500 ppm, 800 ppm, 0.1 wt %, 0.5 wt %, 1 wt %, 2 wt %, 3 wt %, 4 wt %, and 5 wt %. Similarly, the concentration of the C12+ component in FEEDA may vary quite significantly, from 1 ppm to 10 wt %. Non-limiting examples of concentration of the C12+ component, which may be the lower limit and/or the upper limit of a range the actual concentration of the C12+ component may fall within, include 1 ppm, 5 ppm, 10 ppm, 30 ppm, 50 ppm, 80 ppm, 100 ppm, 200 ppm, 500 ppm, 800 ppm, 1000 ppm, 3000 ppm, 5000 ppm, 8000 ppm, 1 wt %, 3 wt %, 5 wt %, 8 wt %, and 10 wt %.

In step (B), FEEDA is subjected to fractionation, wherein the heavy components, typically those with high boiling points, especially the C12+ component, are enriched in the lower effluent EFFBB. An upper effluent, EFFUB, comprising enriched cyclohexanone, methylcyclopentanone and phenol, which all comprise 6 carbon atoms and tend to have lower boiling points than the C12+ component, is produced. It is highly desired that the C12+ component concentration in EFFUB is low, e.g., below 50 ppm (based on the weight of EFFUB), such that the feed material for step (D) prepared from EFFUB, FEEDC, has a low C12+ component concentration. Non-limiting examples of C12+ component concentration in EFFUB, which may be the upper limit or the lower limit of a range thereof in which the actual C12+ component concentration may fall, include: 1000 ppm, 800 ppm, 600 ppm, 500 ppm, 400 ppm, 200 ppm, 100 ppm, 80 ppm, 60 ppm, 50 ppm, 40 ppm, 30 ppm, 20 ppm, 10 ppm, 5 ppm, 3 ppm, 1 ppm, 0.5 ppm and even 0.1 ppm, based on the weight of EFFUB. In certain highly desirable embodiments, the C12+ component concentration in EFFUB is below detection limit using the measurement method as commonly employed in commercial operations (e.g., gas chromatography). The C12+ component in the lower effluent EFFBB may be recycled and reused in another process, such as a transalkylation and/or dealkylation process.

In step (C), at least part of EFFUB, desirably the entirety of EFFUB in certain embodiments, is used to form a feed FEEDC, which is subjected to fractionation according to the processes of the present disclosure. FEEDC comprises cyclohexanone at a concentration CHXN(1), methylcyclopentanone at a concentration CMCP(1), phenol at a concentration CPhol(1), and water at a concentration CH2O(1), all based on the weight of FEEDC, where CH2O(1)≥0.10 wt %. CHXN(1), CMCP(1), CPhol(1) and CH2O(1) may be the same or different from the concentration of cyclohexanone, methylcyclopentanone, phenol and water, respectively, in EFFUB. In one particularly desirable embodiment, CHXN(1), CMCP(1) and CPhol(1) are substantially the same as the concentrations of cyclohexanone, methylcyclopentanone and phenol, respectively, in EFFUB. In certain embodiments, CH2O(1) is substantially the same as the water concentration in EFFUB and no additional water is introduced into FEEDC. In certain other embodiments, additional water is intentionally added into FEEDC, resulting in CH2O(1) appreciably higher than the water concentration in EFFUB. Such additional amount of water may be combined with other components such as cyclohexanone, methylcyclopentanone and phenol, and the whole mixture is charged as a single feedstock mixture into the second fractionation column. Alternatively, at least part of the additional water may be added into the second fractionation column at a location separate and different from the location(s) where at least a portion of the other components of FEEDC are charged into the second fractionation column. In one particularly advantageous embodiment, a separate water stream is fed into the second separation column at a location between the bottom of the second separation column and the location where the rest of FEEDC is fed into the second separation column. In this embodiment, due to the lower boiling point of water than cyclohexanone and methylcyclopentanone and phenol, the added water in the separate water stream will travel upwards in the vapor phase and have sufficient time to contact the other components of FEEDC as they travel downwards and/or upwards, thereby facilitating the separation of methylcyclopentanone from cyclohexanone and phenol.

Water concentration in FEEDC, CH2O(1), may range from, e.g., 0.10 wt % to 10 wt %, based on the total weight of FEEDC, regardless of whether water is combined with other components of FEEDC in a single inflow stream, or a water stream separate and independent from stream(s) of other components is used as part of FEEDC source as indicated above. Non-limiting examples of CH2O(1), which may be the upper limit and/or the lower limit of a range of water concentration in which the actual CH2O(1) falls, include: 0.10 wt %, 0.2 wt %, 0.3 wt %, 0.4 wt %, 0.5 wt %, 0.6 wt %, 0.7 wt %, 0.8 wt %, 0.9 wt %, 1.0 wt %, 1.2 wt %, 1.4 wt %, 1.6 wt %, 1.8 wt %, 2.0 wt %, 2.2 wt %, 2.4 wt %, 2.6 wt %, 2.8 wt %, 3.0 wt %, 3.2 wt %, 3.4 wt %, 3.6 wt %, 3.8 wt %, 4.0 wt %, 4.2 wt %, 4.4 wt %, 4.6 wt %, 4.8 wt %, 5.0 wt %, 6.0 wt %, 7.0 wt %, 8.0 wt %, 9.0 wt %, and 10.0 wt %. When CH2O(1) is lower than 0.10 wt %, its impact on methylcyclopentanone separation efficiency is sub-optimal. Experiments showed that at 1.0 wt % CH2O(1), the increase of methylcyclopentanone separation can be dramatic compared to the situation without added water. Adding water at amount over 5.0 wt % of FEEDC results in quite substantial consumption of water in step (D), adding to the cost of the equipment and process. The water added into step (D) typically exits the manufacture process as waste water comprising other contaminants mandating cleaning treatment. Therefore, adding an excessive amount of water into FEEDC, e.g., at over 5.0 wt %, is best avoided. In addition, the amount of water included in FEEDC depends on the methylcyclopentanone concentration in FEEDC, CMCP(1), and the required methylcyclopentanone concentration in EFFBD, CMCP(3), described in greater detail below.

In FEEDC, similar to in FEEDA, the concentration of cyclohexanone, CHXN(1), may vary quite significantly, e.g., from 10 wt % to 99 wt %, based on the total weight of FEEDC. Non-limiting examples of CHXN(1), which may be the lower limit and/or upper limit of a range the actual CHXN(1) may fall within, include 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, and 99 wt %.

In FEEDC, similar to FEEDA, the concentration of methylcyclopentanone CMCP(1) may vary quite significantly as well, e.g., from 1 ppm to 5 wt %. Desirably, CMCP(1) in FEEDA is not higher than 5 wt %. Non-limiting examples of CMCP(1), which may be the lower limit and/or upper limit of a range the actual CMCP(1) may fall within, include 1 ppm, 5 ppm, 10 ppm, 50 ppm, 100 ppm, 500 ppm, 800 ppm, 0.1 wt %, 0.5 wt %, 1 wt %, 2 wt %, 3 wt %, 4 wt %, and 5 wt %. In certain highly desirable embodiments, CMCP(1) is at most 600 ppm, e.g., at most 400 ppm, at most 300 ppm, at most 200 ppm, at most 100 ppm, or even at most 80 ppm. As discussed above, the separation of methylcyclopentanone from cyclohexanone using conventional fractionation distillation is challenging given the close boiling points between these compounds, especially where a high purity of cyclohexanone is desired and the separation and removal of very small concentration of methylcyclopentanone from cyclohexanone is the objective of the fractionation distillation. The invention of the present disclosure is particularly advantageous and economical for removing such small amounts of methylcyclopentanone from cyclohexanone to obtain a cyclohexanone product with high purity. It is known that methylcyclopentanone may be present in the cyclohexanone product stream at a relatively low concentration, e.g., below 1 wt %, made in a phenol and cyclohexanone manufacture process using oxidation of cyclohexylbenzene followed by cleavage, where the cyclohexylbenzene is made by hydroalkylation of benzene. As such, the process according to the present disclosure is particularly advantageous for purifying the cyclohexanone product made in this process, as described in greater detail below.

Phenol has a relatively high boiling point (182° C. at 101 kPa) compared to cyclohexanone (156° C. at 101 kPa) and methylcyclopentanone. It is known that phenol and cyclohexanone form an azeotrope with about 72 wt % of phenol and about 28 wt % cyclohexanone at a boiling point below that of cyclohexanone. In many industrial processes for making cyclohexanone, phenol is present at various amounts in the mixture of cyclohexanone and methylcyclopentanone subjected to methylcyclopentanone removal. In certain embodiments, in step (C), CPhol(1)≥XX wt %, where XX may be: 5; 10; 15; 20; 25; 30; 35; or even 40. In certain desired embodiments, CPhol(1)≤YY wt %, where YY may be: 45; 40; 35; 30; 25; 20; or even 15. Non-limiting examples of CPhol(1), which may be the lower limit and/or upper limit of a range the actual CPhol(1) may fall within, include 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, and 95 wt %.

In certain highly desirable embodiments, the concentration of the C12+ component in FEEDC is below detection limit using the measurement method as commonly employed in commercial operations (e.g., gas chromatography).

In step (D), FEEDC is subjected to fractionation in a second fractionation column to produce an upper effluent EFFUD comprising cyclohexanone at a concentration CHXN(2), methylcyclopentanone at a concentration CMCP(2), phenol at a concentration CPhol(2) and water at a concentration CH2O(2), and a lower effluent EFFBD comprising cyclohexanone at a concentration CHXN(3), methylcyclopentanone at a concentration CMCP(3), phenol at a concentration CPhol(3) and water at a concentration CH2O(3). CHXN(2), CMCP(2), CPhol(2) and CH2O(2) are all based on the weight of EFFUD. CHXN(3), CMCP(3), CPhol(3) and CH2O3(3) are all based on the weight of EFFBD. Due to a high boiling point, phenol is enriched in EFFBD, and thus typically CPhol(3)>CPhol(1)>CPhol(2). Due to a relatively low boiling point, methylcyclopentanone is enriched in EFFUD, and thus typically CMCP(2)>CMCP(1)>CMCP(3). In certain embodiments, CHXN(3)>CHXN(1)>CHXN(2); in other embodiments, CHXN(2)>CHXN(1)>CHXN(3).

In certain highly desired embodiments of the processes of the present disclosure, substantially all methylcyclopentanone is removed from FEEDC in EFFUD, resulting in a very low CMCP(3) in the EFFBD. For example, in certain embodiments CMCP(3)≤XX ppm, where XX may be: 100; 90; 80; 70; 60; 50; 40; 35; 30; 20; 15; 10; 8; 5; 3; 1.0; 0.5; 0.3; or even 0.1. In these embodiments, EFFBD is essentially a mixture of phenol and cyclohexanone with a high purity. This mixture may be subjected to extractive distillation, described in greater details below.

Due to the high boiling point of phenol compared to cyclohexanone, methylcyclopentanone and water, phenol is enriched in the lower effluent EFFBD and desirably deficient in the upper effluent EFFUD. Thus, in certain embodiments, CPhol(2)≤10.0 ppm, in certain embodiments CPhol(2)≤5.0 ppm, in certain embodiments CPhol(2)≤1.0 ppm, in certain embodiments CPhol(2)≤0.5 ppm. The lower effluent EFFBD may comprise, in addition to phenol, substantial amount of cyclohexanone, which may be separated in an extractive distillation step afterwards, as described below.

As a result of the relatively high concentration of CH2O(1) in FEEDC, i.e., CH2O(1)≥0.10 wt %, the separation of methylcyclopentanone from the mixture of methylcyclopentanone, cyclohexanone and phenol in FEEDC may be conducted at a high efficiency in a second separation column with a relatively small number of theoretical trays N, where 1≤N≤80. Examples of the number of theoretical trays N in the second separation column, which may be the lower limit and/or upper limit of a range of N, the actual N may fall within, include 1, 5, 10, 15, 20, 25, 30, 35, 40, 45, 50, 55, 60, 65, 70, 75, and 80. A smaller number of theoretical trays N as a result of the processes of the present disclosure may result in a relatively short fractionation column that is significantly less expensive to construct and maintain due to less material consumption, less energy required for the operation, and lower probability of failure as a result of the simplicity.

In conventional fractionation columns for separating methylcyclopentanone from a feedstock mixture of methylcyclopentanone and cyclohexanone, due to the relative close boiling points of cyclohexanone and methylcyclopentanone, as discussed above, the fractionation typically is required to run at a vacuum such as at most ZZ kPa, where ZZ may be: 50; 40; 30; 20; 15; or even 10. In the processes of the present disclosure, as a result of the increased fractionation efficiency due to the inclusion of significant amount of water in FEEDC, i.e., CH2O(1)≥0.10 wt %, one may operate the fractionation step (D) at a higher pressure that is otherwise impracticable. For example, in certain embodiments, the fractionation step (D) of the process according to the present disclosure may be conducted at an internal absolute pressure in a range from a lower limit P1 kPa to an upper limit of 101 kPa, where P1 may be: 30; 40; 50; 60; 70; 80; or even 90. In addition, because the processes of the present disclosure do not require the employment of special equipment different from those used in conventional fractionation processes, vacuum pressure, such as an absolute internal pressure of at most ZZ kPa, where ZZ may be: 50; 40; 30; 20; 15; or even 10, may be used as well.

In certain embodiments, CMCP(2)/CMCP(1)≥R1, where R1 may be: 3.0; 5.0; 08.0; 10.0; 15.0; 20.0; 25.0; 30.0; 50.0; 80.0; 100; 150; 200; 300; 500; or even 800. In certain particularly desirable embodiments, due to the high distillation efficiency enabled by the inclusion of higher water concentration in FEEDC, and the use of a relative large number of theoretical trays in the second separation column (e.g., where N≥30, or N≥50, or N≥60, or even N≥70), CMCP(2)/CMCP(1)≥R2, where R2 may be: 1000; 2000; 5000; 8000; or even 10,000. In certain embodiments, CMCP(1)/CMCP(3)≥R1, where R1 may be: 3.0; 5.0; 8.0; 10.0; 15.0; 20.0; 25.0; 30.0; 50.0; 80.0; 100; 150; 200; 300; 500; or even 800. In certain particularly desirable embodiments, due to the high distillation efficiency enabled by the inclusion of higher water concentration in FEEDC, and the use of a relative large number of theoretical trays in the second separation column (e.g., where N≥30, or N≥50, or N≥60, or even N≥70), CMCP(1)/CMCP(3)≥R3, where R3 may be: 1000; 2000; 5000; 8000; or even 10,000. In certain desirable embodiments, CMCP(3)≤R4 ppm, where R4 may be: 100; 80; 60; 40; 20; 10; 8; 5; 3; 1; 0.8; 0.5; 0.3; or even 0.1. In certain other highly desirable embodiments, CMCP(3) is below detection limit using the detecting method as commonly employed in commercial operations (e.g., gas chromatography).

Water has a boiling point lower than that of methylcyclopentanone, cyclohexanone and phenol. As a result, a great majority of the water included in FEEDC will exit the second separation column in an upper effluent. In highly desired embodiments of the process according to the present disclosure, the water concentration CH2O(3) in the lower effluent EFFBD is so low such that CH2O(3)≤R5 ppm, where R5 may be: 100; 80; 60; 40; 20; 10; 8; 5; 3; 1; 0.8; 0.5; 0.3; or even 0.1. In certain other highly desirable embodiments, CH2O(3) is below detection limit using the detecting method as commonly employed in commercial operations (e.g., gas chromatography).

Part of the upper effluent EFFUD in step (D) may be recycled as a reflux stream into the second separation column to achieve a higher level of separation of methylcyclopentanone from cyclohexanone and phenol. In the processes of the present disclosure, as a result of the significantly improved separation efficiency conferred in part by the relatively high water concentration in FEEDC, a high degree of separation may be achieved without the use of a large reflux ratio. Thus, in certain desired embodiments, in step (D), the reflux ratio at the second separation column is at most RR, where RR may be: 20; 15; 10; 8; 5; 3; 1; 0.5; 0.1; 0.05; or even 0.03.

To achieve the desired separation efficiency in step (D), the temperature of the upper effluent EFFUD may vary in a range, e.g., from 5° C. to 80° C., and the temperature of the lower effluent EFFBD may vary in a range, e.g., from 90° C. to 200° C. Non-limiting examples of the temperature of EFFUD, which may be the lower limit and/or upper limit of a range the actual temperature may fall within, include 5° C., 10° C., 15° C., 20° C., 25° C., 30° C., 35° C., 40° C., 45° C., 50° C., 55° C., 60° C., 65° C. and 70° C. Non-limiting examples of the temperature of EFFBD, which may be the lower limit and/or upper limit of a range the actual temperature may fall within, include 90° C., 100° C., 110° C., 120° C., 130° C., 140° C., 150° C., 160° C., 170° C., 180° C., 190° C., and 200° C.

In certain embodiments of the process according to the present disclosure, a further step (E) as follows is carried out:
(E) fractionating a feed mixture FEEDE comprising at least a portion of the lower effluent EFFBD in a third separation column to obtain a cyclohexanone-rich upper effluent EFFUE and a phenol-rich lower effluent EFFBE.

Due to the removal of methylcyclopentanone in the fractionation step (D), the cyclohexanone-rich upper effluent EFFUE is desirably deficient in methylcyclopentanone. In certain embodiments, EFFUE has a methylcyclopentanone concentration CMCP(4), where CMCP(4)≤AA ppm, where AA may be: 100; 80; 50; 40; 30; 10; 8; 6; 4; 2; 1; 0.5; 0.3; or even 0.1. Desirably, CMCP(4) is so low that it is undetectable using the measurement method as commonly employed in commercial operations (e.g., gas chromatography).

As discussed above, cyclohexanone and phenol may form an azeotrope comprising about 72 wt % of phenol and about 28 wt % of cyclohexanone, making complete separation of a mixture of these two compounds by fractionation without the addition of other reagents impossible. To that end, an extractive solvent, such as a glycol (e.g., 1,2-ethanediol, 1,3-propanediol, 1,4-butanediol, diethylene glycol, dipropylene glycol, dibutylene glycol, and the like) may be included into FEEDE to break the azeotrope enabling a substantially complete separation of cyclohexanone from phenol. In such embodiments, the upper effluent EFFUE may comprise essentially pure cyclohexanone, and the lower effluent EFFBE may comprise a mixture of phenol and the extractive solvent, which may be then separated in a subsequent step using distillation or water extraction. Extractive distillation methods for separating phenol and cyclohexanone are described in co-pending, and co-assigned U.S. Provisional Patent Application Ser. Nos. 61/641,374 and 61/641,375, both filed on May 2, 2012 and entitled "Process for Producing Phenol and Cyclohexanone," the contents of both of which are incorporated herein by reference in their entirety.

In certain embodiments of the process according to the first aspect of the present disclosure, the cyclohexanone material essentially free of methylcyclopentanone in the effluent EFFUE may be further converted at least in part into a product PCapro comprising caprolactam and methylvalerolactam at a concentration CMVAM (including all isomers having formulae (F-I), (F-II), (F-III) and (F-IV) described above), where CMVAM≤BB ppm, where BB may be: 100.0; 80.0; 60.0; 50.0; 40.0; 20.0; 10.0; 8.0; 5.0; 3.0; 1.0; 0.8; 0.5; 0.3; or even 0.1. Desirably, CMVAM is below detection limit using the measurement method as commonly employed in commercial operations (e.g., gas chromatography). The product PCapro may be produced by, e.g., Route-1 discussed above. The high-purity PCapro may be further used for making additional materials, such as high-performance nylon-6 by polymerization discussed above. High-performance nylon-6 fibers are tough, possessing high tensile strength, elasticity and luster. They are wrinkle-proof and highly resistant to abrasion and chemicals such as acids and alkalis. The polymer may be used as thread in bristles for toothbrushes, surgical sutures, and strings for acoustic and classical musical instruments. It is also used in the manufacture of a large variety of threads, ropes, filaments, nets, tire cords, as well as clothes.

As discussed above, FEEDA may be derived from a variety of processes for making phenol and/or cyclohexanone, such as cyclohexane oxidation, phenol hydrogenation, cyclohexylbenzene oxidation followed by cleavage, and the like. In a particularly advantageous embodiment of the process according to the first aspect of the present disclosure, step (A) includes:
(AI) contacting benzene and $H_2$ with a hydroalkylation catalyst under a hydroalkylation condition effective to produce a hydroalkylation effluent comprising cyclohexylbenzene and methylcyclopentylbenzene;
(AII) subjecting at least a portion of the hydroalkylation effluent to oxidation effective to convert at least a portion of the cyclohexylbenzene and methylcyclopentylbenzene into corresponding hydroperoxides thereof;
(AIII) subjecting at least a portion of the hydroperoxides of cyclohexylbenzene and methylcyclopentylbenzene to cleavage to produce a cleavage effluent comprising phenol, cyclohexanone and methylcyclopentanone; and
(AIV) obtaining FEEDA from the cleavage effluent.

A second aspect of the present disclosure is directed to a process for separating methylcyclopentanone from a mixture comprising cyclohexanone and methylcyclopentanone, the process comprising:
(I) providing a first feedstock having a concentration of cyclohexanone CHXN(1) and a concentration of methylcyclopentanone CMCP(1);
(II) including water in the first feedstock at a concentration CH2O(1) of at least 0.10 wt %, based on the total weight of the first feedstock; and
(III) fractionating the first feedstock in a first distillation column to obtain a first upper effluent and a first lower effluent, wherein:
the first upper effluent has a concentration of methylcyclopentanone CMCP(2), a concentration of cyclohexanone CHXN(2), and a water concentration of CH2O(2);
the lower effluent has a concentration of methylcyclopentanone CMCP(3), a concentration of cyclohexanone CHXN (3), and a water concentration of CH2O(3); and
CMCP(2)/CMCP(1)≥3.0.

A non-limiting example of the first feedstock provided in step (I) in the process of the second aspect of the present disclosure is FEEDC in steps (C) and (D) of the process according to the first aspect of the present disclosure, described in detail above. A non-limiting example of the first distillation column in the process of the second aspect of the present disclosure corresponds to the second separation column of step (D) in the process according to the first aspect of the present disclosure, described in detail above. Thus, the above description of the process of the first aspect of the present disclosure may be adapted for the process of the second aspect.

In certain other embodiments of the process according to the second aspect of the present disclosure, the first feedstock provided in step (I) is deficient in phenol. In one embodiment, the first feedstock consists essentially of methylcyclopentanone, water and cyclohexanone. In one embodiment, the first feedstock consists essentially of the upper effluent EFFUD produced in step (D) of the process according to the first aspect of the present disclosure and optionally additional amount of water. In yet another embodiment, step (I) of the process according to the second aspect of the present disclosure comprises:

(IA) contacting benzene and $H_2$ with a hydroalkylation catalyst under a hydroalkylation condition effective to produce a hydroalkylation effluent comprising cyclohexylbenzene and methylcyclopentylbenzene;

(IB) subjecting at least a portion of the hydroalkylation effluent to oxidation effective to convert at least a portion of the cyclohexylbenzene and methylcyclopentylbenzene into corresponding hydroperoxides thereof;

(IC) subjecting at least a portion of the hydroperoxides of cyclohexylbenzene and methylcyclopentylbenzene to cleavage to produce a cleavage effluent comprising phenol, cyclohexanone, and methylcyclopentanone; and (ID) obtaining the first feedstock from the cleavage effluent.

In certain specific embodiments, step (ID) comprises:

(ID1) fractionating at least a portion of the cleavage effluent in a third distillation column to obtain a third upper effluent rich in cyclohexanone and methylcyclopentanone and a third lower effluent rich in phenol and essentially free of methylcyclopentanone; and

(ID2) obtaining the first feedstock from the third upper effluent.

Detailed description of a specific embodiment for making cyclohexanone via cyclohexylbenzene, which may be treated using a process according to the present disclosure, is provided as follows.

Production of Cyclohexylbenzene

In the integrated process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 family molecular sieve, or by oxidative coupling of benzene to make biphenyl followed by hydrogenation of the biphenyl. However, in practice, the cyclohexylbenzene is desirably produced by contacting the benzene with hydrogen under hydroalkylation conditions in the presence of a hydroalkylation catalyst whereby the benzene undergoes the following Route-3 to produce cyclohexylbenzene (CHB):

(Route 3).

For an example of hydroalkylation of benzene in the presence of hydrogen for the production of cyclohexylbenzene, see U.S. Pat. Nos. 6,730,625 and 7,579,511, which are incorporated by reference. Also, see International Application Publications WO2009/131769 or WO2009/128984, directed to catalytic hydroalkylation of benzene in the presence of hydrogen for the production of cyclohexylbenzene.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes molecular sieves having the MWW framework topology. (Such crystal structures are discussed in the "Atlas of Zeolite Framework Types," Fifth edition, 2001, the entire content of which is incorporated as reference).

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal may be employed in the hydroalkylation catalyst, although suitable metals include palladium, ruthenium, nickel, zinc, tin, and cobalt, with palladium being particularly advantageous. Desirably, the amount of hydrogenation metal present in the catalyst is between 0.05 wt % and 10 wt %, such as between 0.10 wt % and 5 wt %, of the catalyst.

Suitable binder materials include synthetic or naturally occurring substances as well as inorganic materials such as clay, silica and/or metal oxides.

Although the hydroalkylation reaction is highly selective towards cyclohexylbenzene, the effluent from the hydroalkylation reaction may contain some dialkylated products, as well as unreacted benzene and the desired monoalkylated species. The unreacted benzene may be recovered by distillation and recycled to the alkylation reactor. The lower effluent from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 $hr^{-1}$ to 10 $hr^{-1}$ on total feed, and a benzene/dicyclohexylbenzene weight ratio of 1:1 to 5:1.

Oxidation of Cyclohexylbenzene

After removal of the unreacted benzene and the polyalkylated benzenes and other heavy species, the cyclohexylbenzene is fed to the oxidation reaction.

As discussed above, the process includes oxidizing at least a portion of a feed comprising cyclohexylbenzene to produce an oxidation composition comprising cyclohexyl-1-phenyl- 1-hydroperoxide. As used herein, "oxidizing" means causing an oxidation reaction to occur.

Regardless of the source or sources, in various embodiments, a feed comprising cyclohexylbenzene contains at least 10 wt %, or at least 25 wt %, or at least 50 wt %, or at least 65 wt %, or at least 75 wt %, or at least 95 wt %, or at least 99 wt % cyclohexylbenzene. In various embodiments, it may contain another component. For example, the feed comprising cyclohexylbenzene may contain at least 1 ppm and no greater than 1 wt % bicyclohexane, or at least 10 ppm and no greater than 8000 ppm bicyclohexane. It may contain at least 1 ppm and no greater than 1 wt % biphenyl, or at least 10 ppm and no greater than 8000 ppm biphenyl. It may contain at least 1 ppm and no greater than 2 wt % methylcyclopentylbenzene, or at least 10 ppm and no greater than 1 wt % methylcyclopentylbenzene as any isomer: 1-phenyl-1-methylcyclopentane, 1-phenyl-2-methylcyclopentane, and 1-phenyl-3-methylcyclopentane. There may be other components present, though desirably of low concentration, say, no greater than 1000 ppm, or no greater than 100 ppm of phenol, olefins or alkylene benzenes such as cyclohexenyl benzene, individually or in any combination. The feed comprising cyclohexylbenzene to which oxygen is introduced to cause an oxidation reaction may contain cyclohexylbenzene, any other one component, or any combination of the other components just noted in the proportions for each or in combination just noted.

In various exemplary embodiments, oxidation may be accomplished by contacting an oxygen-containing gas, such as air and various derivatives of air, with the feed comprising cyclohexylbenzene.

The oxidation may be conducted in the absence or presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI).

In various embodiments, the oxidation reaction occurs under oxidation conditions. Suitable oxidation conditions include a temperature between 70° C. and 200° C., such as 90° C. to 130° C., and a pressure of 50 kPa to 10,000 kPa. A basic buffering agent may be added to react with acidic by-products that may form during the oxidation. In addition, an aqueous phase may be introduced. The reaction may take place in a batch or continuous flow fashion.

Desirably, the product of the oxidation of a feed comprising cyclohexylbenzene, i.e., the oxidation composition, contains at least 5 wt %, such as at least 10 wt %, for example at least 15 wt %, or at least 20 wt % cyclohexyl-1-phenyl-1-hydroperoxide based upon the total weight of the oxidation composition. In other manifestations, the oxidation composition contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation composition. The oxidation composition may further comprise imide catalyst and unreacted cyclohexylbenzene. The invention may include cyclohexylbenzene in the oxidation composition in an amount of at least 50 wt %, or at least 60 wt %, or at least 65 wt %, or at least 70 wt %, or at least 80 wt %, or at least 90 wt %, based upon total weight of the oxidation composition.

In addition, the oxidation composition may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in the cyclohexylbenzene undergoing oxidation. The reactor used for the oxidation of cyclohexylbenzene, i.e., the oxidation reactor, may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel container with a distributor inlet for the oxygen-containing stream in line. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner well known to those skilled in the art.

At least a portion of the oxidation composition may be subjected to a cleavage reaction, which may include all or some fraction of the oxidation composition as directly produced without undergoing any separation (e.g., some fraction resulting from diverting some amount of the oxidation composition as directly produced to another disposition, such as temporary storage). Thus, the at least a portion of the oxidation composition may have the same composition as the oxidation composition. Further, all or some of the oxidation composition as directly produced may undergo one or more separations, and an appropriate product of that separation (or separations), now modified in composition relative the oxidation composition as directly produced, may provide the at least a portion of the oxidation composition subjected to the cleavage reaction.

For example, all or a fraction of the oxidation composition as directly produced may be subjected to high vacuum distillation, to generate a product enriched in unreacted cyclohexylbenzene relative to the oxidation composition, and the at least a portion of the oxidation composition as a residue concentrated in the desired cyclohexyl-1-phenyl-1-hydroperoxide that may be subjected to a cleavage reaction. Cyclohexylbenzene is essentially a diluent in the cleavage reaction and the neutralization reaction, and further is not a good solvent for most acid catalysts, particularly sulfuric acid. However, distinctive from the Hock process described earlier, it is convenient in the present invention that the at least a portion of the oxidation composition that will undergo the cleavage reaction be of the same composition of cyclohexylbenzene as the oxidation composition directly produced. That is to say, it is convenient that the at least a portion of the oxidation composition undergo no concentration of the hydroperoxide(s) before the acid catalyst is introduced to it, because the starting alkylbenzene cyclohexylbenzene has a significantly higher normal boiling point than the starting alkylbenzene cumene that is found in the Hock process. While within the scope of the present invention, any practical separation attempted to concentrate the cyclohexyl-1-phenyl-1-hydroperoxide or other hydroperoxides from cyclohexylbenzene prior to effecting the cleavage reaction likely requires inconvenient very low vacuum pressure distillation equipment, and even then, likely requires very high temperatures that could cause uncontrolled thermal decomposition of the hydroperoxides.

Additionally or alternatively, all or a fraction of the oxidation composition, or all or a fraction of the vacuum distillation residue may be cooled to cause crystallization of the unreacted imide oxidation catalyst, which may then be separated either by filtration or by scraping from a heat exchanger surface used to effect the crystallization, and provide an at least a portion of the oxidation composition reduced or free from imide oxidation catalyst that may be subjected to a cleavage reaction.

As another example, all or a fraction of the oxidation composition as produced may be subjected to water washing and then passage through an adsorbent, such as a 3 Å molecular sieve, to separate water and other adsorbable compounds, and provide an at least a portion of the oxidation composition with reduced water or imide content that may be subjected to a cleavage reaction. Similarly, all or a fraction of the oxidation composition may undergo a chemically or physically based adsorption, such as passage over a bed of sodium carbonate to remove the imide oxidation catalyst (e.g., NHPI) or other adsorbable components, and provide an at least a portion of the oxidation composition reduced in oxidation catalyst or other adsorbable component content that may be subjected to a cleavage reaction. Another possible separation involves contacting all or a fraction of the oxidation composition as produced with a liquid containing a base, such as an aqueous solution of an alkali metal carbonate or hydrogen carbonate, to form an aqueous phase comprising a salt of the imide oxidation catalyst, and an organic phase reduced in imide oxidation catalyst provided as an at least a portion of the oxidation composition that may be subjected to a cleavage reaction.

Cleavage Reaction

As discussed above, the process includes cleaving at least a portion of the oxidation composition in the presence of an acid catalyst to produce a cleavage reaction mixture comprising the acid catalyst, phenol, and cyclohexanone. As used herein, "cleaving" means causing a cleavage reaction to occur. In the cleavage reaction, at least a portion of the desired cyclohexyl-1-phenyl-1-hydroperoxide will decompose in high selectivity to cyclohexanone and phenol, and further, any other hydroperoxides present will decompose to various products, discussed below.

In various embodiments, the acid catalyst is at least partially soluble in the cleavage reaction mixture, stable at a temperature of at least 185° C. and has a lower volatility (higher normal boiling point) than cyclohexylbenzene. In various embodiments, the acid catalyst is also at least partially soluble in the treated cleavage reaction mixture.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (ppm) and no greater than 3000 ppm of the acid catalyst, or at least 150 ppm to and no greater than 2000 ppm of the acid catalyst, or at least 300 ppm and no greater than 1500 ppm of the acid catalyst, based upon total weight of the cleavage reaction mixture.

In various embodiments of the processes of the present invention, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

In various embodiments, the cleavage reaction occurs under cleavage conditions. Suitable cleavage conditions include a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

Conversion of any hydroperoxide, such as cyclohexyl-1-phenyl-1-hydroperoxide, and conveniently all cyclohexyl-1-phenyl-1-hydroperoxide and other hydroperoxides, may be very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide and other hydroperoxides present in the at least a portion of the oxidation composition undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone, each of which may comprise 40 wt % to 60 wt %, or 45 wt % to 55 wt % of the cleavage reaction mixture, such wt % based on the weight of the cleavage reaction mixture exclusive of unreacted cyclohexylbenzene and acid catalyst.

The cleavage reaction mixture may comprise no greater than 30 wt %, or no greater than 25 wt %, or no greater than 15 wt % of phenol, or it may comprise at least 1 wt %, or at least 3 wt %, or at least 5 wt %, or at least 10 wt % phenol, based on total weight of the cleavage reaction mixture. Further, the cleavage reaction mixture may comprise no greater than 30 wt %, or no greater than 25 wt %, or no greater than 15 wt % of cyclohexanone, or it may comprise at least 1 wt %, or at least 3 wt %, or at least 5 wt %, or at least 10 wt % cyclohexanone, based on total weight of the cleavage reaction mixture.

The cleavage reaction mixture may further comprise at least 0.1 wt % and no greater than 10 wt %, or at least 0.5 wt % and no greater than 7 wt %, or at least 1 wt % and no greater than 5 wt %, or at least 1.5 and no greater than 3 wt % of any one or combination of contaminant byproducts based on the total weight of the cleavage reaction mixture.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture or the neutralized cleavage mixture or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation composition from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

Contaminant Treatment

As discussed above, the cleavage reaction mixture may comprise one or more contaminants. In various embodiments disclosed herein, the processes further comprise contacting at least a portion of a contaminant with an acidic material to convert at least a portion of the contaminant to a converted contaminant, thereby producing a modified reaction mixture.

Suitable acidic material for use in treating the cleavage reaction product include microporous acidic materials, such as zeolites, aluminas and aluminosilicates, especially zeolites having a pore diameter over 4 Angstrom; cation exchange resins, especially sulfonic resins, such as Rohm & Haas Amberlyst 16; Bronsted acids, such as formic acid acetic acid, hydrochloric acid and sulfuric acid; sulfurous acid or salts thereof, such as sodium sulfate, sodium hydrogen bisulfate and sodium metabisulfite; and aqueous acid solutions. In one embodiment, the acidic material used to treat the cleavage reaction product comprises at least part of the acid catalyst used to promote the cleavage reaction.

Conveniently, the acidic material has a relatively low volatility, with a normal boiling point above phenol and/or cyclohexylbenzene, such that it will tend to distill in the lower product in subsequent fractionation operations that may be conducted.

The contaminant treatment may be conducted directly on the cleavage reaction mixture, or after one or more separations of the cleavage reaction mixture. For example, the cleavage reaction mixture may be separated (e.g., by distillation) into phenol-rich and cyclohexanone-rich fractions before or after the contaminants are subjected to contaminant treatment.

Suitable contaminant treatment conditions vary with the acidic material employed. Treatment conditions include a temperature of at least 30° C., or at least 35° C., or at least 40° C., or at least 50° C., or at least 60° C., or at least 70° C., or at least 80° C., or at least 90° C., or at least 100° C. In various embodiments, the temperature is less than 250° C., or less than 225° C., or less than 190° C., or less than 180° C., or less than 170° C., or less than 160° C., or less than 150° C., or less than 140° C. The temperature may be any range of the aforementioned temperatures.

The pressure may be 0.75 psig to 500 psig (5 kPa to 3450 kPa), or 10 psig to 200 psig (70 kPa to 1380 kPa) such that the cleavage reaction mixture is completely or predominantly in the liquid phase during the treatment.

In various embodiments, the pressure may be 10 psig to 200 psig (170 kPa to 1380 kPa) and the temperature may be 60° C. to 160° C., such that most of the cleavage reaction mixture is in the liquid phase.

In embodiments in which the acidic material is a solid microporous material (e.g., zeolites, aluminas, etc.), the pressure may be 10 psig to 200 psig (70 kPa to 1380 kPa) and the temperature may be 100° C. to 250° C., such that most of the cleavage reaction mixture is in the liquid phase.

In various embodiments in which the acidic material is an cation exchange resins, the pressure may be 10 psig to 200 psig (70 kPa to 1380 kPa) and the temperature may be 30° C. to 100° C., such that most of the cleavage reaction mixture is in the liquid phase.

It will be understood that the contaminants in all or a portion of the cleavage reaction mixture may be contacted with an acidic material as disclosed herein. For example, contaminants in a distilled fraction of the entire cleavage reaction mixture containing an enriched or depleted concentration of phenol and/or cyclohexanone relative to the cleavage reaction mixture may be contacted with an acidic material as described herein. When a stream is described as being "enriched" in a specified species, it is meant that the wt % of the specified species in that stream is enriched relative to the feed stream prior to separation. When a stream is described as being "depleted" in a specified species, it is meant that the wt % of the specified species in that stream is reduced relative to the feed stream prior to separation.

Additionally or alternatively, a filtered fraction of the entire cleavage reaction mixture with reduced amounts of filterable components may be contacted with an acidic material as described herein.

Additionally or alternatively, a fraction of the cleavage reaction mixture has undergone an absorption operation, such as a water wash, such that absorbable components are reduced in concentration prior to contact with an acidic material.

Additionally or alternatively, a fraction of the cleavage reaction mixture has undergone an adsorption operation, such as passing over a molecular sieve to remove water (e.g., a 3 Å molecular sieve) with one or more adsorbable components are reduced in concentration prior to contact with an acidic material.

The contaminant reactor may be any vessel that allows contacting of the contaminant with an acidic material for a suitable residence time. For example, a contaminant reactor may be an open or substantially open vessel reactor or pipe.

In various embodiments, a process for making phenol and cyclohexanone comprises: (i) cleaving a stream comprising cyclohexyl-1-phenyl-1-hydroperoxide in the presence of an acidic cleavage catalyst to produce a cleavage reaction mixture comprising phenol, cyclohexanone, acidic cleavage catalyst, and one or more contaminants; (ii) reacting at least a portion of the acidic cleavage catalyst with a basic material to form a neutralized stream; (iii) separating the neutralized stream into one or more streams rich in cyclohexanone, phenol and/or cyclohexylbenzene, relative to the neutralized stream; and (iv) contacting one or more of the cyclohexanone-rich portion, the phenol-rich portion, and the cyclohexylbenzene-rich portion with an acidic material to remove one or more contaminants.

In various embodiments, the cleavage reaction mixture is separated into: (1) an overhead product that comprises greater than 98 wt %, or greater than 99 wt %, of cyclohexanone, based upon total weight of the overhead product; and (2) a lower product comprising phenol and cyclohexanone in azeotropic proportion. The impurities contained in the overhead product may include methylcyclopentanone. As used herein, "azeotropic proportion" means 65 wt %-75 wt % phenol and 23 wt %-35 wt % cyclohexanone, or 72 wt % phenol and 28 wt % cyclohexanone, based upon total weight of the stream. In various embodiments, a portion or the entire cleavage reaction mixture may be combined with another stream from the overall phenol production process. For example, the cleavage reaction mixture may be combined with a stream containing cyclohexanone produced by the hydrogenation of phenol. Additionally or alternatively, the cleavage reaction mixture may be combined with a stream containing phenol that is produced by the dehydrogenation of cyclohexanone. Additionally or alternatively, the cleavage reaction mixture may be combined with one or more additives, such as an antifoam or surfactant agent.

In various embodiments, contaminants in more than one portion of the cleavage reaction mixture may be contacted with an acidic material. For example, the cleavage reaction mixture may be separated into one or more streams rich in cyclohexanone, phenol and/or cyclohexylbenzene, relative to the cleavage reaction mixture and each stream may be contacted with an acidic material. The acidic material may be the same or different for each fraction.

In various embodiments, a given fraction of the cleavage reaction mixture may undergo more than one contacting steps with an acidic material. For example, a cyclohexanone-rich fraction derived from distillation of the entire cleavage reaction mixture may first be contacted with a first acidic material (e.g., sulfuric acid) and then separately exposed to a second acidic material (e.g., a cation exchange resin).

Processing of Treated Cleavage Reaction Mixture

In various embodiments, after one or more contaminants in the cleavage reaction mixture is contacted with an acidic material, the stream may be separated into one or more streams rich in phenol, cyclohexanone and/or cyclohexylbenzene, relative to the feed stream. These streams may be substantially or completely free of contaminants.

In various exemplary embodiments, the process further comprises separating the contaminant-treated stream into a first stream that is enriched in cyclohexanone or phenol or both and a second stream that is enriched in converted contaminant relative to the contaminant-treated stream.

Heat Treatment

In various embodiments, some or all of the contaminants (e.g., in the cleavage reaction mixture or some portion of the cleavage reaction mixture) are subjected to heat treatment conditions upstream or downstream of the contaminant treatment.

For example, the temperature of all or a portion of the cleavage reaction mixture may be raised to at least 100° C., or 150° C. to 185° C., or at least 200° C. to produce a heat-treated cleavage reaction mixture. In various embodiments, the temperature may be less than 250° C., or less than 225° C. The temperature may be any range of the aforementioned temperatures. In various embodiments, the heat treatment conditions include a residence time may be at least 1 min., 2 min., 3 min., 5 min., 10 min., or 15 min. The residence time may be less than 120 min., 60 min., or 30 min. The residence time may be any logical range of the aforementioned times.

In one embodiment, during heat treatment at least 1 wt %, or 10.0 wt %, or 20.0 wt %, or 50.0 wt %, or 80.0 wt %, or 90.0 wt %, or 99.0 wt %, or 99.9 wt %, or all of any one contaminant (e.g., hydroxycyclohexanone, or other oxyketones such as hexanophenone, 6-hydroxyhexanophenone, 6-hydroperoxyhexanophenone, benzoic acid, pentanal, pentanone, 2-hydroxycyclohexanone, phenylcyclohexanone, or unreacted peroxides) is converted to a converted contaminant.

In various embodiments, no greater than 80.0 wt %, or 50.0 wt %, or 30.0 wt %, or 20.0 wt %, or 10.0 wt % of contaminant hydroxycyclohexanone or other oxyketones, such as 6-hydroxyhexanophenone, or both are converted to a converted contaminant including a furan with both an olefin and oxygen moiety, such as 1,2,4a,9b-tetrahydrodibenzo[b,d]furan that may result from the dehydration, alkylation, and cyclization reaction of phenol and hydroxycyclohexanone.

In various embodiments, the heat-treated stream may be separated into one or more streams rich in one or more of cyclohexanone, phenol, and/or cyclohexylbenzene, relative to the heat-treated stream. These fractions may comprise little or no converted contaminants.

The heat treatment may be conducted in a simple vessel or pipe, which may be open or have means for mixing, such as baffles or a static mixer for turbulent flow. Further, the heat treatment may take place in a fractionation column, wherein fractionation operating conditions are selected such that the components distilled are exposed to the temperatures and residence times noted at any point or points in the column. The heat treated components may be withdrawn from any point in the fractionation column, as an overhead, lower or side composition product. In certain embodiments, the heat treatment converts at least some of the contaminants or converted contaminants to other compounds more readily removed from the phenol and/or cyclohexanone.

After contaminant treatment and/or heat treatment or combined contaminant and heat treatment, the converted contaminants may desirably have a property that makes them more separable from phenol or cyclohexanone, or both, than the starting contaminant. Separable can be distillable, e.g., the converted contaminant does not form an azeotrope with phenol or cyclohexanone whereas the starting contaminant does, and/or filterable, and/or absorbable. As a result, following contaminant and/or heat treatment, the stream may be subjected to one or more separations ultimately resulting in streams that predominantly comprise cyclohexanone, phenol and converted contaminant.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid and/or plasticizers.

Description According to the Drawings

The invention will now be more particularly described with reference to the accompanying drawings.

Figure 1:
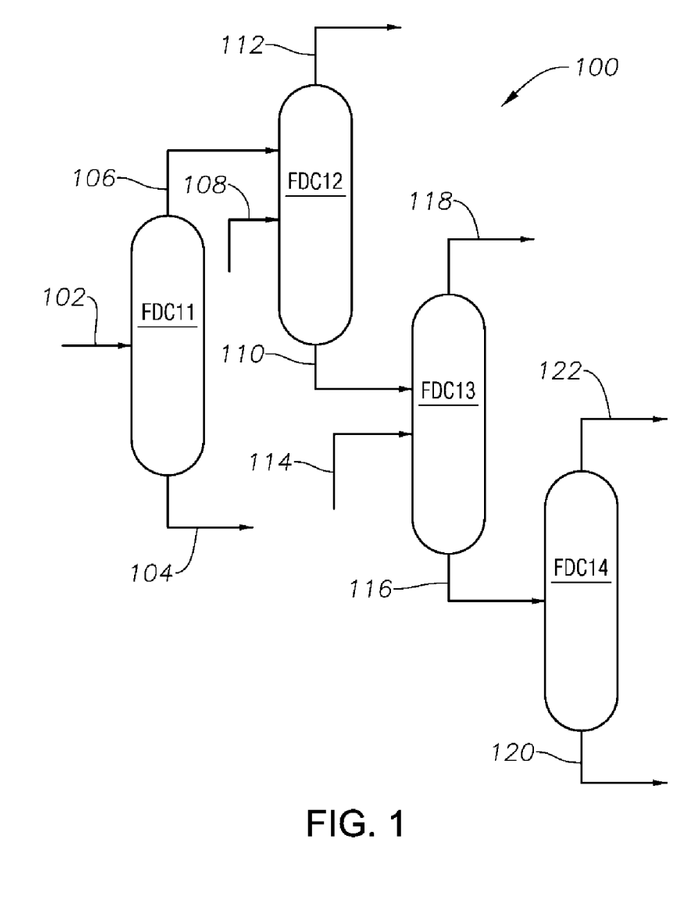
FIGS. 1 and 2 are schematic flow diagrams illustrating two different embodiments of the process according to the present disclosure comprising a step of separating methylcyclopentanone from a mixture of cyclohexanone, methylcyclopentanone, and phenol.

Referring to FIG. 1, a process 100 is shown in which a feedstock 102 comprising cyclohexanone, methylcyclopentanone, phenol and a C12+ component is fed into a fractionation distillation column FDC11, where a lower effluent 104 rich in the C12+ component is produced and an upper effluent 106 rich in C6 such as cyclohexanone, methylcyclopentanone and phenol is obtained. The effluent 106, along with a stream of water 108, is subsequently fed into a fractionation distillation column FDC12, where a process according to the present disclosure is conducted to obtain a lower effluent 110 rich in phenol and cyclohexanone and an upper effluent 112 rich in methylcyclopentanone. The concentration of methylcyclopentanone in effluent 112 is significantly higher than in effluent 106. Effluent 112 may comprise a certain amount of cyclohexanone. The effluent 112 may be sent to a downstream fractionation distillation column where the cyclohexanone and methylcyclopentanone is further separated according to the processes of the present disclosure (not shown). Alternatively, effluent 112 may be discarded. Effluent 110 is then fed into a fractionation distillation column FDC13 along with a stream 114 of an extractive solvent such as diethyleneglycol, where an upper effluent 118 rich in cyclohexanone and a lower effluent 116 rich in phenol and the extractive solvent are produced. The effluent 118 is essentially pure cyclohexanone free of methylcyclopentanone and phenol. The effluent 116 is then fed into a vacuum fractionation distillation column FDC14, where a lower effluent 120 rich in the extractive solvent and an upper effluent 122 consisting essentially of phenol are obtained. The substantially pure cyclohexanone stream 118 may be then sent directly to the next step, where it is converted to, e.g., high-purity caprolactam which may be used for making high-performance nylon-6 material.

Figure 2:
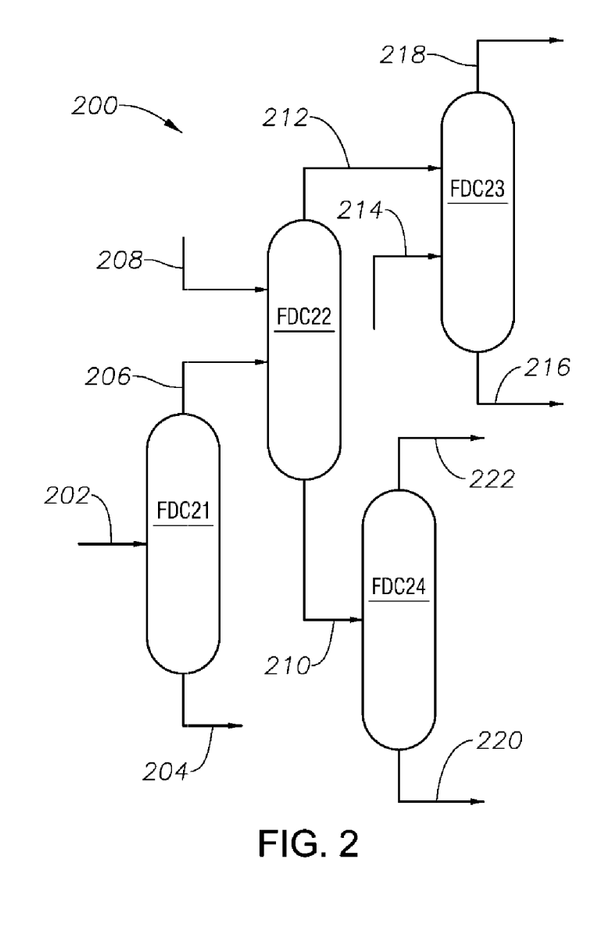

In FIG. 2, a process 200 is shown in which a feedstock 202 comprising cyclohexanone, methylcyclopentanone, phenol and a C12+ component is fed into a fractionation distillation column FDC21, where a lower effluent 204 rich in the C12+ component is produced and an upper effluent 206 rich in C6 such as cyclohexanone, methylcyclopentanone and phenol is obtained. The effluent 206, along with a stream 208 of extractive solvent such as diethylene glycol, is fed into a fractionation distillation column FDC22, where a lower effluent 210 rich in phenol and the extractive solvent and an upper effluent 212 rich in cyclohexanone and methylcyclopentanone are produced. The effluent 212 along with a water stream 214 is then fed into a vacuum distillation column FDC23 having an absolute internal pressure of 50 kPa, where a process according to the present disclosure is conducted to obtain a lower effluent 216 consisting essentially of cyclohexanone and an upper effluent 218 rich in methylcyclopentanone. Similar to the embodiment of FIG. 1, the water stream 214 is introduced into FDC23 at a location between the bottom of FDC23 and the location where effluent 212 is fed into FDC23 to allow for sufficient contact between the added water and methylcyclopentanone and cyclohexanone. The pure cyclohexanone effluent stream 216 may be sent directly to the next step, where it is converted into, e.g., caprolactam. The lower effluent 210 flowing from FDC22, rich in the extractive solvent and phenol, is fed into a vacuum fractionation distillation column FDC24, where a lower effluent 220 rich in the extractive solvent and an upper effluent 222 consisting essentially of pure phenol are obtained.

The feedstock 102 and 202 may be produced by the cleavage of a stream comprising a hydroperoxide of cyclohexylbenzene and a hydroperoxide of methylcyclopentylbenzene, such as in the process described in detail in WO2012/036822A1, the relevant content of which is incorporated herein in its entirety.

EXAMPLES

Two experiments were carried out using the equipment corresponding to FIG. 1 except that, rather than injecting water separately through line 108, water was incorporated directly in the feed stream 106. The feed stream 106 in both examples comprised phenol in a range of 45-48 wt %, cyclohexanone in a range of 45-48 wt %, and methylcyclopentanone. Methylcyclopentanone concentrations in the feed stream 106 and effluent streams 110 and 112 are indicated in TABLE I below. In Example 1, a comparative example, no water was included into the feed 106. In Example 2, water was included in the feed 106 at a concentration of 1.0 wt % based on the total weight of the feed 106 (including water). Fractionation in FDC12 was carried out in both experiments at an absolute internal pressure of 10.3 kPa, a lower effluent 110 temperature of 165° C. and an upper effluent 112 temperature of 90° C. The distillation column, having 60-80 theoretical plates, was packed with ⅛" (3.4 mm) random packing.

TABLE I

| | Methylcyclopentanone concentration (ppm) | | | | |
|---|---|---|---|---|---|
| | Feed Stream 106 (CMCP(1)) | Effluent 112 (CMCP(2)) | Effluent 110 (CMCP(3)) | CMCP(2)/CMCP(1) | CMCP(1)/CMCP(3) |
| Example 1 (comparative) | 30 | 192 | 27 | 6.4 | 1.1 |
| Example 2 (inventive) | 150 | 13800 | 3 | 92.0 | 50.0 |

It is quite clear from the data in TABLE I that the addition of water at 1.0 wt % dramatically increased the separation efficiency of methylcyclopentanone from the feed mixture 106: the CMCP(2)/CMCP(1) ratio increased from 6.4 to 92.0; the CMCP(1)/CMCP(3) ratio increased from only 1.1 to 50.0; and the CMCP(3) reduced from 27 ppm to merely 3 ppm, even though the feed 106 in Example 2 had a much higher CMCP(1) to begin with.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. The contents of all references mentioned herein are incorporated by reference in their entirety.

Non-limiting embodiments of the processes of the present disclosure include:

E1. A process for separating methylcyclopentanone from a mixture comprising cyclohexanone, and methylcyclopentanone, the process comprising:

(I) providing a first feedstock having a concentration of cyclohexanone CHXN(1) and a concentration of methylcyclopentanone CMCP(1);

(II) including water in the first feedstock at a concentration CH2O(1) of at least 0.10 wt %, based on the total weight of the first feedstock; and (III) fractionating the first feedstock in a first distillation column to obtain a first upper effluent and a first lower effluent, wherein: the first upper effluent has a concentration of methylcyclopentanone CMCP(2), a concentration of cyclohexanone CHXN(2), and a water concentration of CH2O(2); the lower effluent has a concentration of methylcyclopentanone CMCP(3), a concentration of cyclohexanone CHXN(3), and a water concentration of CH2O(3); and CMCP(2)/CMCP(1) ≥3.0.

E2. The process according to embodiment E1, wherein the first distillation column comprises N theoretical trays, where 1≤N≤80, or 1≤N≤70, or 1≤N≤60, or 1≤N≤50, or 1≤N≤40, or 1≤N≤30, or 1≤N≤20, or 1≤N≤10.

E3. The process according to embodiment E2 or embodiment E3, wherein the absolute pressure inside the first distillation column is at most P0 kPa, where P0 in various embodiments can be: 101; 80; 70; 60; 50; 40; 30; 20; 10; or even 5.

E4. The process according to any of the preceding embodiments E1 to E3, wherein the absolute pressure inside the first distillation column is at least P1 kPa, where P1 in various embodiments can be: 5; 10; 20; 30; 40; 50; 60; 70; or even 80.

E5. The process according to any of the preceding embodiments E1 to E4, wherein CMCP(2)/CMCP(1)≥R1, where R1 may be: 4.0; 5.0; 8.0; 10.0; 15.0; 20.0; 25.0; 30.0; 50.0; 80.0; 100; 150; 200; 300; 500; 800; 1000; 2000; 4000; 5000; 8000; or even 10,000.

E6. The process according to any of the preceding embodiments E1 to E5, wherein CMCP(1)/CMCP(3)≥R1, where R1 may be: 3.0; 5.0; 8.0; 10.0; 15.0; 20.0; 25.0; 30.0; 50.0; 80.0; 100; 150; 200; 300; 500; 800; 1000; 2000; 5000; 8000; or even 10,000.

E7. The process according to any of the preceding embodiments E1 to E6, wherein CH2O(1)≥XX wt %, where XX in various embodiments may be: 0.2; 0.4; 0.5; 0.6; 0.8; 1.0; 1.2; 1.4; 1.5; 1.6; 1.8; 2.0; 2.5; 3.0; 3.5; 4.5; 4.0; 5.0.

E8. The process according to any of the preceding embodiments E1 to E7, wherein CH2O(1)≤YY wt %, where YY in various embodiments may be: 6.0; 5.5; 5.0; 4.5; 4.0; 3.5; 3.0; 2.5; 2.0.

E9. The process according to any of the preceding embodiments E1 to E8, wherein CMCP(1)≥ZZ ppm, where ZZ in various embodiments may be: 10; 20; 40; 60; 80; 100; 150; 200; 250; 300; 350; 400; 450; 500; 600; 800; 1000; 2000; 3000; 4000; 5000.

E10. The process according to any of the preceding embodiments E1 to E9, wherein CMCP(3)≤R3 ppm, where R3 in various embodiments may be: 100; 80; 60; 40; 20; 10; 8; 5; 3; 1; 0.8; 0.5; 0.3; or even 0.1.

E11. The process according to any of the preceding embodiments E1 to E10, wherein CMCP(1)≤AA, where AA in various embodiments may be: 5.0 wt %; 3.0 wt %; 2.0 wt %; 1.0 wt %; 0.5 wt %; 0.1 wt %; 0.05 wt %; 0.01 wt %; 5000 ppm; 1000 ppm; 800 ppm; 500 ppm; or even 300 ppm.

E12. The process according to any of the preceding embodiments E1 to E11, wherein in step (III), the reflux ratio at the distillation column is at most RR, where RR in various embodiments can be: 20; 15; 10; 5; 1; 0.5; 0.1; or even 0.05.

E13. The process according to any of the preceding embodiments E1 to E12, wherein:

in step (I), the first feedstock further comprises phenol at a concentration CPhol(1), where CPhol(1)≥1 wt %; and in step (III), the first upper effluent has a phenol concentration of CPhol(2), where CPhol(2)≤XX ppm, where XX in various embodiments can be: 10.0; 8.0; 6.0; 5.0; 4.0; 2.0; 1.0; or even 0.5.

E14. The process according to embodiment E13, wherein: CPhol(1)≥40 wt %.

E15. The process according to any of the preceding embodiments E1 to E14, wherein:

in step (I), the concentration of phenol in the first feedstock is CPhol(1), where CPhol(1)≤1.0 ppm.

E16. The process according to any of the preceding embodiments E1 to E15, further comprising the following step (IV):

(IV) fractionating at least a portion of the first lower effluent in a second distillation column to obtain a cyclohexanone-rich second upper effluent and a phenol-rich second lower effluent.

E17. The process according to embodiment E16, wherein: in step (IV), an extractive solvent is added into the first lower effluent fed into the second distillation column.

E18. The process according to any of the preceding embodiments E1 to E17, wherein step (I) comprises:

(IA) contacting benzene and $H_2$ with a hydroalkylation catalyst under a hydroalkylation condition effective to produce a hydroalkylation effluent comprising cyclohexylbenzene and methylcyclopentylbenzene;

(IB) subjecting at least a portion of the hydroalkylation effluent to oxidation effective to convert at least a portion of the cyclohexylbenzene and methylcyclopentylbenzene into corresponding hydroperoxides thereof;

(IC) subjecting at least a portion of the hydroperoxides of cyclohexylbenzene and methylcyclopentylbenzene to cleavage to produce a cleavage effluent comprising phenol, cyclohexanone and methylcyclopentanone; and (ID) obtaining the first feedstock from the cleavage effluent.

E19. The process according to embodiment E18, wherein step (ID) comprises:

(ID1) fractionating at least a portion of the cleavage effluent in a third distillation column to obtain a third upper effluent rich in cyclohexanone and methylcyclopentanone and a third lower effluent rich in phenol and essentially free of methylcyclopentanone; and (ID2) obtaining the first feedstock from the third upper effluent.

E20. The process according to any of the preceding embodiments E1 to E19, further comprising the following step:

(V) subjecting the first upper effluent to a separation operation to obtain a recycle water stream; and (VI) feeding the recycle water stream into the first feedstock in step (II).

E21. The process according to any of the preceding embodiments E1 to E20, wherein in step (II), at least a portion of the water is included into the first feedstock before the first feedstock is fed into the first distillation column.

E22. The process according to any of the preceding embodiments E1 to E21, wherein in step (II), substantially all of the water is included into the first stock before the first stock is fed into the first distillation column.

E23. The process according to any of the preceding embodiments E1 to E21, wherein in step (II), at least a portion of the water is included into the first feedstock as a separate water stream into the first distillation column.

E24. The process according to embodiment E23, wherein the location where the separate water stream is fed into the first distillation column is between the location where the rest of the first feedstock is fed into the first column and the bottom of the first distillation column.

E25. The process according to any of the preceding embodiments E1 to E24, wherein in step (III): the temperature of the first upper effluent is from 5° C. to 80° C.; or from 10° C. to 70° C.; or from 20° C. to 60° C.; or from 30° C. to 50° C.

E26. The process according to any of the preceding embodiments E1 to E25, wherein in step (III): the temperature of the first lower effluent is from 90° C. to 200° C.; or from 100° C. to 190° C.; or from 110° C. to 180° C.; or from 120° C. to 170° C.; or from 130° C. to 160° C.; or from 140° C. to 150° C.

E27. The process according to any of the preceding embodiments E1 to E26, wherein CH2O(1) and CH2O(2) are such that the total amount of water included in the first feedstock in step (II) is substantially equal to the total amount of water contained in the first upper effluent.

E28. The process according to any of the preceding embodiments E1 to E27, further comprising the following step:
(VII) converting at least a portion of the cyclohexanone in the first lower effluent into a product PCapro comprising caprolactam and methylvalerolactam at a concentration CMVAM, where CMVAM≤5.0 ppm, or CMVAM≤3.0 ppm, or CMVAM≤1.0 ppm, or CMVAM≤0.8 ppm, or CMVAM≤0.5 ppm, or CMVAM≤0.3 ppm.

E29. A process for separating methylcyclopentanone from a mixture comprising cyclohexanone and methylcyclopentanone, the process comprising:
(A) providing a feed FEEDA comprising:
cyclohexanone at a concentration CHXN(A); methylcyclopentanone at a concentration CMCP(A),
phenol at a concentration of CPhol(A), and
a C12+ component;
(B) fractionating FEEDA in a first separation column to obtain:
an upper effluent EFFUB comprising cyclohexanone, methylcyclopentanone and phenol; and
a lower effluent EFFBB comprising at least a portion of the C12+ component;
(C) providing a feed FEEDC from at least a portion of EFFUB, FEEDC comprising water at a concentration CH2O(1) of at least 0.10 wt %, cyclohexanone at a concentration of CHXN(1), methylcyclopentanone at a concentration CMCP(1), and phenol at a concentration CPhol(1); and
(D) fractionating FEEDC in a second separation column to obtain:
an upper effluent EFFUD comprising cyclohexanone at a concentration CHXN(2), methylcyclopentanone at a concentration CMCP(2), phenol at a concentration CPhol(2), and water at a concentration of CH2O(2); and
a lower effluent EFFBD comprising cyclohexanone at a concentration CHXN(3), methylcyclopentanone at a concentration CMCP(3), water at a concentration CH2O(3), and phenol at a concentration CPhol(3).

E30. The process according to E29, wherein in step (D), CMCP(3)≤R3 ppm, where R3 may be: 100; 80; 60; 40; 20; 10; 8; 5; 3; 1; 0.8; 0.5; 0.1; or even 0.1.

E31. The process according to an of the preceding embodiments E29 or E30, wherein the second separation column comprises N theoretical trays, where 1≤N≤80, in certain embodiments 1≤N≤70, in certain embodiments 1≤N≤60, in certain embodiments 1≤N≤50, in certain embodiments 1≤N≤40, in certain embodiments 1≤N≤30.

E32. The process according to any of the preceding embodiments E29 to E31, wherein the absolute pressure inside the second separation column is at most P0 kPa, where P0 in various embodiments may be: 101; 80; 60; 50; 30; 20; 10; or even 5.

E33. The process according to any of the preceding embodiments E29 to E32, wherein the absolute pressure inside the second separation column is at least P1 kPa, where P1 in various embodiments may be: 1; 5; 10; 20; 40; 60; or even 80.

E34. The process according to any of the preceding embodiments E29 to E33, wherein CMCP(2)/CMCP(1)≥R1, where R1 may be: 3.0; 5.0; 8.0; 10.0; 15.0; 20.0; 25.0; 30.0; 50.0; 80.0; 100; 150; 200; 300; 500; 800; 1000; 2000; 4000; 5000; 8000; or even 10,000.

E35. The process according to any of the preceding embodiments E29 to E34, wherein, CMCP(1)/CMCP(3)≥R1, where R1 may be: 3.0; 5.0; 8.0; 10.0; 15.0; 20.0; 25.0; 30.0; 50.0; 80.0; 100; 150; 200; 300; 500; 800; 1000; 2000; 5000; 8000; or even 10,000.

E36. The process according to any of the preceding embodiments E29 to E35, wherein CH2O(1)≥XX wt %, where XX in various embodiments may be: 0.2; 0.4; 0.5; 0.6; 0.8; 1.0; 1.2; 1.4; 1.5; 1.6; 1.8; 2.0; 2.5; 3.0; 3.5; 4.0; 4.5; 5.0.

E37. The process according to any of the preceding embodiments E29 to E36, wherein CH2O(1)≤YY wt %, where YY in various embodiments may be: 6.0; 5.5; 5.0; 4.5; 4.0; 3.5; 3.0; 2.5; 2.0.

E38. The process according to any of the preceding embodiments E29 to E37, wherein CMCP(1)≥ZZ ppm, where ZZ in various embodiments may be: 10; 20; 40; 60; 80; 100; 150; 200; 250; 300; 350; 400; 450; 500; 600; 800; 1000; 2000; 3000; 4000; 5000.

E39. The process according to embodiment E38, wherein CMCP(1)≤AA, where AA in various embodiments may be: 3.0 wt %; 2.0 wt %; 1.0 wt %; 0.5 wt %; 0.10 wt %; 0.05 wt %; 0.01 wt %; 5000 ppm; 1000 ppm; 800 ppm; 500 ppm; 300 ppm.

E40. The process according to any of the preceding embodiments E29 to E39, wherein in step (D), the reflux ratio at the second separation column is at most RR, where RR in various embodiments may be: 20; 15; 10; 5; 1; 0.5; 0.1; 0.05; 0.03.

E41. The process according to any of the preceding embodiments E29 to E40, wherein: in step (C), CPhol(1)≥1 wt %; and in step (D), CPhol(2)≤C2 ppm, where C2 in various embodiments may be: 10.0; 5.0; 1.0; 0.5.

E42. The process according to any of the preceding embodiments E29 to E41, wherein, in step (A):
CHXN(A)≥C1 wt %, where C1 in various embodiments may be: 40; 50; 60; 70; 80; 90;
1 ppm≤CMCP(A)≤10 wt %; or 10 ppm≤CMCP(A)≤8 wt %; or 20 ppm≤CMCP(A)≤7 wt %; or 30 ppm≤CMCP(A)≤6 wt %; or 50 ppm≤CMCP(A)≤5 wt %; or 50 ppm≤CMCP(A)≤1 wt %; and
CPhol(A)≥C3 wt %, where C3 in various embodiments may be: 5; 10; 20; 30; 40.

E43. The process according to E42, further comprising the following step (E):
(E) fractionating a feed mixture FEEDE comprising at least a portion of the lower effluent EFFBD in a third separation column to obtain a cyclohexanone-rich upper effluent EFFUE and a phenol-rich lower effluent EFFBE.

E44. The process according to E43, wherein in step (E), the feed mixture FEEDE comprises an extractive solvent adapted for breaking the azeotrope between cyclohexanone and phenol.

E45. The process according to any of the preceding embodiments E29 to E44, wherein in FEEDA in step (A), the C12+ component has a concentration CHeavy, 5 ppm≤CHeavy≤10 wt %, or 10 ppm≤CHeavy≤8 wt %, or 20 ppm≤CHeavy≤6 wt %, or 30 ppm≤CHeavy≤5 wt %, or 40 ppm≤CHeavy≤4 wt %, or 50 ppm≤CHeavy≤3 wt %, or 60 ppm≤CHeavy≤2 wt %, or 80 ppm≤CHeavy≤1 wt %, or 100 ppm≤CHeavy≤1 wt %.

E46. The process according to any of the preceding embodiments E29 to E45, wherein step (A) comprises: (AI) contacting benzene and $H_2$ with a hydroalkylation catalyst under a hydroalkylation condition effective to produce a hydroalkylation effluent comprising cyclohexylbenzene and methylcyclopentylbenzene; (AII) subjecting at least a portion of the hydroalkylation effluent to oxidation effective to convert at least a portion of the cyclohexylbenzene and methylcyclopentylbenzene into corresponding hydroperoxides thereof; (AIII) subjecting at least a portion of the hydroperoxides of cyclohexylbenzene and methylcyclopentylbenzene to cleavage to produce a cleavage effluent comprising phenol, cyclohexanone and methylcyclopentanone; and (AIV) obtaining FEEDA from the cleavage effluent.

E47. The process according to any of the preceding embodiments E29 to E46, wherein in step (C), at least a portion of the water is included into FEEDC feed before FEEDC is fed into the second separation column.

E48. The process according to any of the preceding embodiments E29 to E47, wherein in step (C) and step (D), substantially all of the water is included into FEEDC before FEEDC is fed into the second separation column in step (D).

E49. The process according to any of the preceding embodiments E29 to E47, wherein in step (C) and step (D), at least a portion of the water is included into FEEDC as a separate water stream into the second separation column.

E50. The process according to embodiment E49, wherein the location where the separate water stream is fed into the second separation column is between the location where the rest of FEEDC is fed into the second separation column and the bottom of the second separation column.

E51. The process according to any of the preceding embodiments E29 to E50, wherein in step (D): wherein in step (III): the temperature of the first upper effluent is in a range from 5° C. to 80° C.; or from 10° C. to 70° C.; or from 20° C. to 60° C.; or from 30° C. to 50° C.

E52. The process according to any of the preceding embodiments E29 to E51, wherein in step (D): the temperature of the first lower effluent is in a range from 90° C. to 200° C.; or from 100° C. to 190° C.; or from 110° C. to 180° C.; or from 120° C. to 170° C.; or from 130° C. to 160° C.; or from 140° C. to 150° C.

E53. The process according to any of the preceding embodiments E29 to E52, wherein in step (C) and step (D), CH2O(1) and CH2O(2) are such that the total amount of water included in FEEDC is substantially equal to the total amount of water contained in the upper effluent EFFUD.

E54. The process according to embodiment E43, further comprising the following step (F):
(F) converting at least a portion of the cyclohexanone in EFFUE into a product PCapro comprising caprolactam and methylvalerolactam at a concentration CMVAM, where CMVAM≤5.0 ppm, or CMVAM≤3.0 ppm, or CMVAM≤1.0 ppm, or CMVAM≤0.8 ppm, or CMVAM≤0.5 ppm, or CMVAM≤0.3 ppm.

The invention claimed is:

1. A process for separating methylcyclopentanone from a mixture comprising cyclohexanone and methylcyclopentanone, the process comprising:
   (I) providing a first feedstock comprising cyclohexanone and methylcyclopentanone, the methylcyclopentanone having a concentration CMCP(1);
   (II) including water in the first feedstock at a concentration CH2O(1) of at least 0.10 wt %; and
   (III) fractionating the first feedstock in a first distillation column to obtain a first upper effluent rich in methylcyclopentanone having a methylcyclopentanone concentration of CMCP(2) and a first lower effluent rich in cyclohexanone, wherein CMCP(2)/CMCP(1)>3.0.

2. The process according to claim 1, wherein the first distillation column comprises N theoretical trays, where 1≤N≤80.

3. The process according to claim 1, wherein CMCP(2)/CMCP(1)≥20.0.

4. The process according to claim 1, wherein the first lower effluent has a methylcyclopentanone concentration CMCP(3), and CMCP(1)/CMCP(3)≥10.0.

5. The process according to claim 1, wherein the first lower effluent has a methylcyclopentanone concentration of less than 20 ppm.

6. The process according to claim 1, wherein CH2O(1)≤6.0 wt %.

7. The process according to claim 1, wherein 10 ppm≤CMCP(1)≤5 wt %.

8. The process according to claim 1, wherein the distillation column in step (III) has a reflux ratio of at most 20.

9. A process for separating methylcyclopentanone from a mixture comprising cyclohexanone and methylcyclopentanone, the process comprising:
   (A) providing a feed FEEDA comprising cyclohexanone, methylcyclopentanone, phenol, and a C12+ component;
   (B) fractionating FEEDA in a first separation column to obtain:
      an upper effluent EFFUB comprising cyclohexanone, methylcyclopentanone and phenol, and
      a lower effluent EFFBB comprising at least a portion of the C12+ component;
   (C) providing a feed FEEDC from at least a portion of EFFUB, FEEDC comprising water at a concentration CH2O(1) of at least 0.10 wt %, cyclohexanone, methylcyclopentanone at a concentration CMCP(1), and phenol; and
   (D) fractionating FEEDC in a second separation column to obtain:
      an upper effluent EFFUD rich in methylcyclopentanone, and
      a lower effluent EFFBD comprising cyclohexanone and phenol.

10. The process according to claim 9, wherein in step (D), EFFBD has a methylcyclopentanone concentration of at most 20 ppm.

11. The process according to claim 9, wherein the second separation column comprises N theoretical trays, where 1≤N≤80.

12. The process according to claim 9, wherein the absolute pressure inside the second separation column is in a range from 1 kPa to 101 kPa.

13. The process according to claim 9, wherein in step (D), EFFUD has a methylcyclopentanone concentration CMCP(2), CMCP(2)/CMCP(1)≥3.0.

14. The process according to claim 9, wherein CH2O(1)≤6.0 wt %.

15. The process according to claim 9, wherein CMCP(1)≥10 ppm.

16. The process according to claim 15, wherein CMCP(1)≤5 wt %.

17. The process according to claim 9, wherein the second separation column in step (D) has a reflux ratio of at most 20.

18. The process according to claim 9, wherein in step (D), the lower effluent has a phenol concentration of at least 1.0 wt %, and the process further comprises the step (E):
(E) fractionating a feed mixture FEEDE comprising at least a portion of the lower effluent EFFBD in a third separation column to obtain a cyclohexanone-rich upper effluent EFFUE and a phenol-rich lower effluent EFFBE.

19. The process according to claim 18, wherein in step (E), the feed mixture FEEDE comprises an extractive solvent adapted for breaking an azeotrope between cyclohexanone and phenol.

20. The process according to claim 9, wherein step (A) comprises:
(AI) contacting benzene and hydrogen with a hydroalkylation catalyst under a hydroalkylation condition effective to produce a hydroalkylation effluent comprising cyclohexylbenzene and methylcyclopentylbenzene;
(AII) subjecting at least a portion of the hydroalkylation effluent to oxidation effective to convert at least a portion of the cyclohexylbenzene and methylcyclopentylbenzene into corresponding hydroperoxides thereof;
(AIII) subjecting at least a portion of the hydroperoxides of cyclohexylbenzene and methylcyclopentylbenzene to cleavage to produce a cleavage effluent comprising phenol, cyclohexanone and methylcyclopentanone; and
(AIV) obtaining FEEDA from the cleavage effluent.

21. The process according to claim 9, wherein in step (C), at least a portion of the water is added into FEEDC before FEEDC is fed into the second separation column.

22. The process according to claim 9, wherein in step (C) and step (D), at least a portion of the water is included into FEEDC as a separate water stream into the second separation column, and the location where the separate water stream is fed into the second separation column is between the location where at least a part of the rest of FEEDC is fed into the second separation column and the bottom of the second separation column.

23. The process according to claim 9, wherein the temperature of the upper effluent EFFUD in step (D) is in a range from 5° C. to 80° C.

24. The process according to claim 9, wherein the temperature of the lower effluent EFFBD in step (D) is in a range from 90° C. to 200° C.

25. The process according to claim 18, further comprising step (F):
(F) converting at least a portion of the cyclohexanone in EFFUE into a product comprising caprolactam and methylvalerolactam at a concentration CMVAM, where CMVAM≤10.0 ppm.

* * * * *